US008541602B2

(12) United States Patent
Takeda et al.

(10) Patent No.: US 8,541,602 B2
(45) Date of Patent: Sep. 24, 2013

(54) COMPOUND, ORGANIC SEMICONDUCTOR MATERIAL, AND SEMICONDUCTOR DEVICE

(75) Inventors: Kodai Takeda, Nisshin (JP); Kenji Nakamura, Anjo (JP); Kenji Takigawa, Nishio (JP)

(73) Assignee: DENSO CORPORATION, Kariya (JP)

( * ) Notice: Subject to any disclaimer, the term of this patent is extended or adjusted under 35 U.S.C. 154(b) by 1 day.

(21) Appl. No.: 13/233,089

(22) Filed: Sep. 15, 2011

(65) Prior Publication Data
US 2012/0088921 A1    Apr. 12, 2012

(30) Foreign Application Priority Data

Sep. 24, 2010   (JP) ................................. 2010-214161

(51) Int. Cl.
*C07D 495/04*    (2006.01)
(52) U.S. Cl.
USPC ........................................... 549/41; 549/456
(58) Field of Classification Search
USPC .................................................. 549/41, 456
See application file for complete search history.

(56) References Cited

U.S. PATENT DOCUMENTS

2009/0043113 A1* 2/2009 Park et al. ...................... 549/41

FOREIGN PATENT DOCUMENTS

| JP | A-2008-147256 | 6/2008 |
|---|---|---|
| JP | A-2009-009965 | 1/2009 |
| JP | A-2009-070986 | 4/2009 |
| JP | A-2009-73780 | 4/2009 |
| JP | A-2010-109360 | 5/2010 |
| JP | A-2010-177641 | 8/2010 |
| JP | A-2010-177643 | 8/2010 |

OTHER PUBLICATIONS

Masahiro Funahashi et al., "Anomalous high carrier mobility in smectic *E* phase of a 2- phenylnaphthalene derivative," *Applied Physics Letters*, vol. 73, No. 25, Dec. 21, 1998, pp. 3733-3735.*
Tunca, A.A., et al. "Investigation on the Condensation of Dialdehydes with 2-Naphthol, 2-Thionaphthol and Dihydroxynaphthalenes." Tetrahedron. vol. 51, No. 7 (1995), pp. 2109-2116.*
Laatsch, H. "3',4'-Dihydro-4,6'dimethoxyspiro[naphthalin-2(1H), 2'-[2H]-naphtho[1,2-b]pyran]-1-on; Bildung und Thermolyseprodukte eines ungewohnlichen Spirochinolethers." Liebigs Annalen der Chemie. vol. 10, (1982), pp. 1808-1828.*
Angelo. "Chalcogen." <http://web.archive.org/web/20090312103521/http://www.angelo.edu/faculty/kboudrea/periodic/periodic_main6.htm>. Mar. 12, 2009.*
Shirota, Y. "Organic materials for electronic and optoelectronic devices." J. Mater. Chem., vol. 10 (2000), pp. 1-25.*
Yen-Yi Lin et al., "Pentacene-Based Organic Thin-film Transistors," *IEEE Transactions on Electron Device*, vol. 44, No. 8, Aug. 1997, pp. 1325-1331.
Masahiro Funahashi et al., "Photoconductive Anisotropy in Smectic Liquid Crystalline Photoconductor, 2-(4'-Octylpheny1)-6-dodecyloxynaphthalene," *Jpn. J. Appl. Phys.* vol. 38, Part 2, No. 2A, Feb. 1999, pp. L132-L135.
Valentine G. Nenajdenko, et al., "A New Route to Annulated Oligothiophenes," *Organic Letters*, 2004 vol. 6, No. 20, Jun. 18, 2004, pp. 3437-3439.
Office Action dated Dec. 13, 2012 and mailed on Dec. 18, 2012 in JP Application No. 2010-214161 (and English translation).
Kunugi, Y., "Single Crystal Organic Field-effect Transistors Based on Dinaphthothienothiophene Isomers", *Journal of Photopolymer Science and Technology*, 2010 vol. 23, No. 3, p. 323-326.

* cited by examiner

*Primary Examiner* — Noble Jarrell
*Assistant Examiner* — John S Kenyon
(74) *Attorney, Agent, or Firm* — Posz Law Group, PLC (57) ABSTRACT

A compound is represented by the following formula:

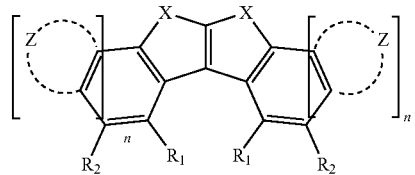

In the formula (1), X is a chalcogen atom. Z is carbon or an aromatic ring structure having at least one sulfur, at least one oxygen, or at least one nitrogen in an aromatic ring to which a substituent is attached. n is an integer of 1 to 3. $R_1$ and $R_2$ are independently selected from a hydrogen atom, a halogen atom, a straight, branched, or cyclic alkyl group, a straight, branched, or cyclic alkoxy group, and a substituted or unsubstituted aryl group.

6 Claims, 6 Drawing Sheets

| | | INITIAL | ROOM TEMPERATURE ONE MONTH LATER |
|---|---|---|---|
| DINAPHTHOTHIENOTHIOPHENE | MOBILITY | 0.23cm$^2$/(Vsec) | 0.21cm$^2$/(Vsec) |
| | THRESHOLD VOLTAGE | -2.3V | -2.5V |
| | ON/OFF RATIO | >10$^6$ | >10$^6$ |
| PENTACENE | MOBILITY | 0.40cm$^2$/(Vsec) | 0.11cm$^2$/(Vsec) |
| | THRESHOLD VOLTAGE | -5.1V | +1.1V |
| | ON/OFF RATIO | >10$^6$ | >10$^4$ |

FIG. 6

| | | INITIAL | 100°C ONE MONTH LATER |
|---|---|---|---|
| DINAPHTHOTHIENOTHIOPHENE | MOBILITY | 0.20cm²/(Vsec) | 0.19cm²/(Vsec) |
| | THRESHOLD VOLTAGE | −2.1V | −1.7V |
| | ON/OFF RATIO | >10⁶ | >10⁶ |
| PENTACENE | MOBILITY | 0.44cm²/(Vsec) | 0.01cm²/(Vsec) |
| | THRESHOLD VOLTAGE | −4.8V | +11.1V |
| | ON/OFF RATIO | >10⁶ | >10³ |

COMPOUND, ORGANIC SEMICONDUCTOR MATERIAL, AND SEMICONDUCTOR DEVICE

CROSS REFERENCE TO RELATED APPLICATION

This application is based on and incorporates herein by reference Japanese Patent Application No. 2010-214161 filed on Sep. 24, 2010.

FIELD OF THE INVENTION

The present invention relates to a compound, an organic semiconductor material, and a semiconductor device.

BACKGROUND OF THE INVENTION

A high-temperature process and a high-vacuum process are essential to form a thin film of silicon, which is an inorganic semiconductor material conventionally used in a semiconductor device. Due to the need of the high-temperature process, it is impossible to form a thin film of silicon on a plastic substrate. Therefore, it is difficult to add flexibility to a product incorporating a semiconductor device and to reduce the weight of the product. Further, due to the need of the high-vacuum process, it is difficult to increase the area of the product and to reduce the cost of the product.

In recent years, research has been actively conducted to develop an organic semiconductor device using an organic semiconductor material. Examples of an organic semiconductor device include an organic thin-film transistor, an organic thin-film photoelectric conversion device, and an organic electroluminescent (organic EL) device.

A temperature of a manufacturing process can be considerably reduced when an organic semiconductor material is used as compared to when an inorganic semiconductor material is used. Therefore, an organic semiconductor material can be deposited on a plastic substrate. Further, an organic semiconductor material has a high solubility in solvent and has a good film formation ability. Therefore, a thin film of an organic semiconductor material can be formed by a deposition method, which does not require the high-vacuum process, such as a deposition method using an ink-jet apparatus. Thus, the increase in the area and the reduction in the cost can be achieved (refer to JP-A-2009-73780).

Reported organic semiconductor materials are broadly classified into low molecular type (including oligomer) and high molecular type. For example, it has been reported that an organic field effect transistor (FET) made of pentacene, which is of low molecular type, has high mobility (refer to Yen-Yi Lin, IEEE Transaction on Electron Device, Vol. 44, No8, p. 1325 (1997), which is a non-patent document).

However, pentacene, which forms an organic semiconductor layer, has a high affinity for oxygen. Therefore, if pentacene is stored in the atmosphere, characteristics of pentacene are degraded. As a result, there is a possibility that the organic semiconductor device cannot stably operate. Further, as the temperature is higher, the degradation proceeds at a higher speed. Therefore, heat resistance is also required.

SUMMARY OF THE INVENTION

In view of the above, it is an object of the present invention to provide a compound, an organic semiconductor material, and a semiconductor device having electrical characteristics that are less likely to be degraded at a high temperature in the atmosphere.

According to a first aspect of the present invention, a compound is represented by a formula (1).

[FORMULA 1]

In the formula (1), X is a chalcogen atom. Z is carbon or an aromatic ring structure having at least one sulfur, at least one oxygen, or at least one nitrogen in an aromatic ring to which a substituent is attached. n is an integer of 1 to 3. $R_1$ and $R_2$ are independently selected from a hydrogen atom, a halogen atom, a straight, branched, or cyclic alkyl group, a straight, branched, or cyclic alkoxy group, and a substituted or unsubstituted aryl group.

The compound has good electric characteristics (for example, mobility, threshold voltage, On/Off ratio of a transistor). The electric characteristics are less likely to be degraded, even when the compound is stored in the atmosphere. For example, the compound can be used as an organic semiconductor material.

For example, X in the formula (1) can be oxygen or sulfur, and Z in the formula (1) can be a benzene ring. For example, n (repeating unit of Z) in the formula (1) can be 1. When X is sulfur, Z is a benzene ring, and n is 1, the compound is represented by a formula (4). When X is oxygen, Z is a benzene ring, and n is 1, the compound is represented by a formula (5).

[FORMULA 4]

[FORMULA 5]

An example of the compound can be represented by a formula (2).

[FORMULA 2]

In the formula (2), $R_1$-$R_6$ are independently selected from a hydrogen atom, a halogen atom, a straight, branched, or cyclic alkyl group, a straight, branched, or cyclic alkoxy group, and a substituted or unsubstituted aryl group.

Further, an example of the compound can be represented by a formula (3).

[FORMULA 3]

In the formula (3), $R_1$-$R_6$ are independently selected from a hydrogen atom, a halogen atom, a straight, branched, or cyclic alkyl group, a straight, branched, or cyclic alkoxy group, and a substituted or unsubstituted aryl group.

In the formulas (1)-(5), $R_1$-$R_6$ are preferably selected from a hydrogen atom, a halogen atom, a straight, branched, or cyclic C1-C20 alkyl group, a straight, branched, or cyclic C1-C20 alkoxy group, and a substituted or unsubstituted C4-C20 aryl group. More preferably, $R_1$-$R_6$ are selected from a hydrogen atom, a halogen atom, a straight, branched, or cyclic C1-C16 alkyl group, a straight, branched, or cyclic C1-C16 alkoxy group, and a C6-C20 aryl group.

Throughout the specification, an aryl group is a carbocyclic aromatic group including a phenyl group and a naphthyl group or a heterocyclic aromatic group including a furyl group, a thienyl group, and a bipyridyl group. For example, an aryl substituent can be a halogen atom, a straight, branched, or cyclic C1-C20 alkyl group, a straight, branched, or cyclic C1-C20 alkoxy group, or an aryl group capable of being substituted by the C4-C20 halogen atom, alkyl group, or alkoxy group.

Concrete examples of $R_1$-$R_6$ in the formulas (1)-(5) can be as follows:

a hydrogen atom;

a halogen atom such as a fluorine atom, a chlorine atom, a bromine atom;

a straight, branched, or cyclic alkyl group such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, a 1-methylpentyl group, a 4-methyl-2-pentyl group, a 3,3-dimethylbutyl group, a 2-ethylbutyl group, a n-heptyl group, a 1-methylhexyl group, a cyclohexylmethyl group, a n-octyl group, a tert-octyl group, a 1-methylheptyl group, a 2-ethylhexyl group, a 2-propylpentyl group, a n-nonyl group, a 2,2-dimethylheptyl group, a 2,6-dimethyl-4-heptyl group, a 3,5,5-trimethylhexyl group, a n-decyl group, a n-undecyl group, a 1-methyldecyl group, a n-dodecyl group, a n-tridecyl group, a n-hexylheptyl group, a n-tetradecyl group, a n-pentadecyl group, a n-hexadecyl group, a n-heptadecyl group, a n-octadecyl group, a n-eicosyl group, a cyclopentyl group, a cyclohexyl group, a 4-methylcyclohexyl group, a 4-tert-butylcyclohexyl group, a cycloheptyl group, or a cyclooctyl group;

a straight, branched, or cyclic alkoxy group such as a methoxy group, an ethoxy group, a n-propoxy group, an isopropoxy group, a n-butoxy group, an isobutoxy group, a sec-butoxy group, a n-pentyloxy group, a neopentyloxy group, a cyclopentyloxy group, a n-hexyloxy group, a 3,3-dimethylbutoxy group, a 2-ethylbutoxy group, a cyclohexyloxy group, a n-heptyloxy group, a n-octyloxy group, a 2-ethylhexyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, or a n-eicosyloxy group;

a substituted or unsubstituted aryl group such as a phenyl group, a 2-tolyl group, a 3-tolyl group, a 4-tolyl group, a 4-ethylphenyl group, a 4-n-propylphenyl group, a 4-isopropylphenyl group, a 4-n-butylphenyl group, a 4-isobutylphenyl group, a 4-tert-butylphenyl group, a 4-isopentylphenyl group, a 4-tert-pentylphenyl group, a 4-n-hexylphenyl group, a 4-cyclohexylphenyl group, a 4-n-heptylphenyl group, a 4-n-octylphenyl group, a 4-n-nonylphenyl group, a 4-n-decylphenyl group, a 4-n-undecylphenyl group, a 4-n-dodecylphenyl group, a 4-n-tetradecylphenyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 3,4,5-trimethylphenyl group, a 2,3,4,5-tetramethylphenyl group, a 2,3,5,6-tetramethylphenyl group, a 5-indanyl group, a 1,2,3,4-tetrahydro-5-naphthyl group, a 1,2,3,4-tetrahydro-6-naphthyl group, a 2-methoxyphenyl group, a 3-methoxyphenyl group, a 4-methoxyphenyl group, a 3-ethoxyphenyl group, a 4-ethoxyphenyl group, a 4-n-propoxyphenyl group, a 4-isopropoxyphenyl group, a 4-n-butoxyphenyl group, a 4-isobutoxyphenyl group, a 4-n-pentyloxyphenyl group, a 4-n-hexyloxyphenyl group, a 4-cyclohexyloxyphenyl group, a 4-n-heptyloxyphenyl group, a 4-n-octyloxyphenyl group, a 4-n-nonyloxyphenyl group, a 4-n-decyloxyphenyl group, a 4-n-undecyloxyphenyl group, a 4-n-dodecyloxyphenyl group, a 4-n-tetradecyloxyphenyl group, a 2,3-dimethoxyphenyl group, a 2,4-dimethoxyphenyl group, a 2,5-dimethoxyphenyl group, a 3,4-dimethoxyphenyl group, a 3,5-dimethoxyphenyl group, a 3,5-diethoxyphenyl group, a 2-methoxy-4-tolyl group, a 2-methoxy-5-tolyl group, a 4-methoxy-2-tolyl group, a 4-methoxy-3-tolyl group, a 5-methoxy-3-tolyl group, a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 4-trifluoromethylphenyl group, a 2,4-difluorophenyl group, a 2,4-dichlorophenyl group, a 3,4-dichlorophenyl group, a 3,5-dichlorophenyl group, a 4-chloro-2-tolyl group, a 2-chloro-4-tolyl group, a 3-chloro-4-tolyl group, a 2-chloro-4-methoxyphenyl group, a 4-chloro-3-methoxyphenyl group, a 4-fluoro-3-methoxyphenyl group, a 3-fluoro-4-methoxyphenyl group, a 2,3,4,5,6-pentafluorophenyl group, a 4-phenylphenyl group, a 3-phenylphenyl group, a 4-(4'-tolyl)phenyl group, a 4-(4'-methoxyphenyl)phenyl group, a 1-naphthyl group, a 2-naphthyl group, a 4-methyl-1-naphthyl group, a 4-ethoxy-1-naphthyl group, a 6-n-butyl-2-naphthyl group, a 6-methoxy-2-naphthyl group, a 7-ethoxy-2-naphthyl group, a 1-anthracenyl group, a 2-anthracenyl group, a 9-anthracenyl group, a 2-tetracenyl group, a 2-fluorenyl group, a 9,9-dimethyl-2-fluorenyl group, a 9,9-di-n-propyl-2-fluorenyl group, a 2-furyl group, a 2-thienyl group, a 5-n-propyl-2-thienyl group, a 5-n-butyl-2-thienyl group, a 5-n-hexyl-2-thienyl group, a 5-n-octyl-2-thienyl group, a 5-n-decyl-2-thienyl group, a 5-n-tridecyl-2-thienyl group, a 5-phenyl-2-thienyl group, a 5-(2'-thienyl)-2-thienyl group, a 5-(5'-n-butyl-2'-thienyl)-2-thienyl group, a 5-(5'-n-hexyl-2'-thienyl)-2-thienyl group, a 5-(5'-n-decyl-2'-thienyl)-2-thienyl group, a 3-thienyl group, a 2-pyridyl group, a 3-pyridyl group, or a 4-pyridyl group.

Formulas (6)-(17) represent concrete examples of the compound represented by the formula (2).

(6)

(7)

$H_{2m+1}C_m$ ——— $C_mH_{2m+1}$ m = 1 ~ 20

(8)

$H_{2m+1}C_m$ ——— $C_mH_{2m+1}$ m = 1 ~ 20

(9)

$H_{2m+1}C_m$ ——— $C_mH_{2m+1}$ m = 1 ~ 20

(10)

$H_{2m+1}C_m$ ——— $C_mH_{2m+1}$ m = 1 ~ 20

(11)

$C_mH_{2m+1}$ $C_mH_{2m+1}$ m = 1 ~ 20

-continued (12)

(13)

$C_6H_{13}$ ——— $C_6H_{13}$ (14)

F ——— F (15)

TMS ——— TMS (16)

(17)

According to a second aspect of the present invention, an organic semiconductor material can have any compound described above. The organic semiconductor material can have only the above described compound. Alternatively, the organic semiconductor material can have any addition ingredient in addition to the compound. The organic semiconductor material has good electric characteristics (for example, mobility, threshold voltage, On/Off ratio of a transistor). The electric characteristics are less likely to be degraded, even when the organic semiconductor material is stored in the atmosphere. For example, the compound can be used as an organic semiconductor material. The organic semiconductor material can be used to manufacture a semiconductor device. Examples of the semiconductor device can include a thin-film transistor, a thin-film photoelectric conversion device, and an electroluminescent (organic EL) device. In these examples, an organic semiconductor layer can be made of the organic semiconductor material.

According to a third aspect of the present invention, a semiconductor material has a thin film made of the organic semiconductor material described above. The thin film of the semiconductor device has good electric characteristics (for example, mobility, threshold voltage, On/Off ratio of a transistor). The electric characteristics are less likely to be degraded, even when the organic semiconductor material is stored in the atmosphere. Examples of the semiconductor device can include a thin-film transistor, a thin-film photoelectric conversion device, and an electroluminescent (organic EL) device.

BRIEF DESCRIPTION OF THE DRAWINGS

The above and other objects, features, and advantages will become more apparent from the following description and drawings in which like reference numerals depict like elements. In the drawings.

DETAILED DESCRIPTION OF THE PREFERRED EMBODIMENT

An embodiment of the present invention is described.

1. Synthesis of 2-bromo-1-mercaptonaphthalene 2-bromo-1-mercaptonaphthalene is synthesized by a method shown in FIG. 1. This synthesis method is described in Roczniki Chemii (1965), 39(3), 391-403.

Firstly, a commercial 2-Amino-1-naphthalenesulfonic acid (made by Tokyo Chemical Industry CO., LTD, 50 g) (S1 in FIG. 1) is dissolved in 2.5% aqueous sodium hydroxide, cooled to 0° C., added to sodium nitrite (made by Tokyo Chemical Industry CO., LTD, 15.4 g) dissolved in 50 ml of the purified water, added to concentrated hydrochloric acid (made by Wako Pure Chemical Industries, Ltd, 112 ml), agitated for thirty minutes, and then filtered. Then, the precipitate is washed with 250 ml of the purified water. Then, the filtrate is added to 48% hydrobromic acid (made by Tokyo Chemical Industry CO., LTD, 100 ml) in which copper bromide (made by Wako Pure Chemical Industries, Ltd, 50 g) is suspended, heated to 95° C., and filtered. Then, the filtrate is added to potassium chloride (made by Wako Pure Chemical Industries, Ltd, 50 g), and the precipitate is filtered, dissolved in 65 ml of boiling water, and neutralized and recrystallized in 50% potassium hydroxide solution. Thus, 25 g of 2-bromo-1-naphthalenesulfonic acid potassium salt (S2 in FIG. 1) is obtained.

Then, phosphorus pentachloride (made by Tokyo Chemical Industry CO., LTD, 30 g) is added to S2, heated to 100° C., agitated for thirty minutes, cooled to a room temperature, and agitated for four hours. Then, the reactant is exposed to ice to stop reaction and recrystallized. Thus, 20 g of 2-bromo-1-naphthalenesulfonyl chloride (S3 in FIG. 1) is obtained.

Then, S3 is added to acetic acid (made by Wako Pure Chemical Industries, Ltd, 420 ml) in which stannous chloride dihydrate (made by Wako Pure Chemical Industries, Ltd, 120 g) is dissolved, and agitated for five hours under a room temperature. The reacted solution is added to concentrated hydrochloric acid (420 ml), left for two hours, extracted, and recrystallized. Thus, 2-bromo-1-mercaptonaphthalene (S4 in FIG. 1) is obtained.

2. Synthesis of Dinaphthothienothiophene

Figure 1:
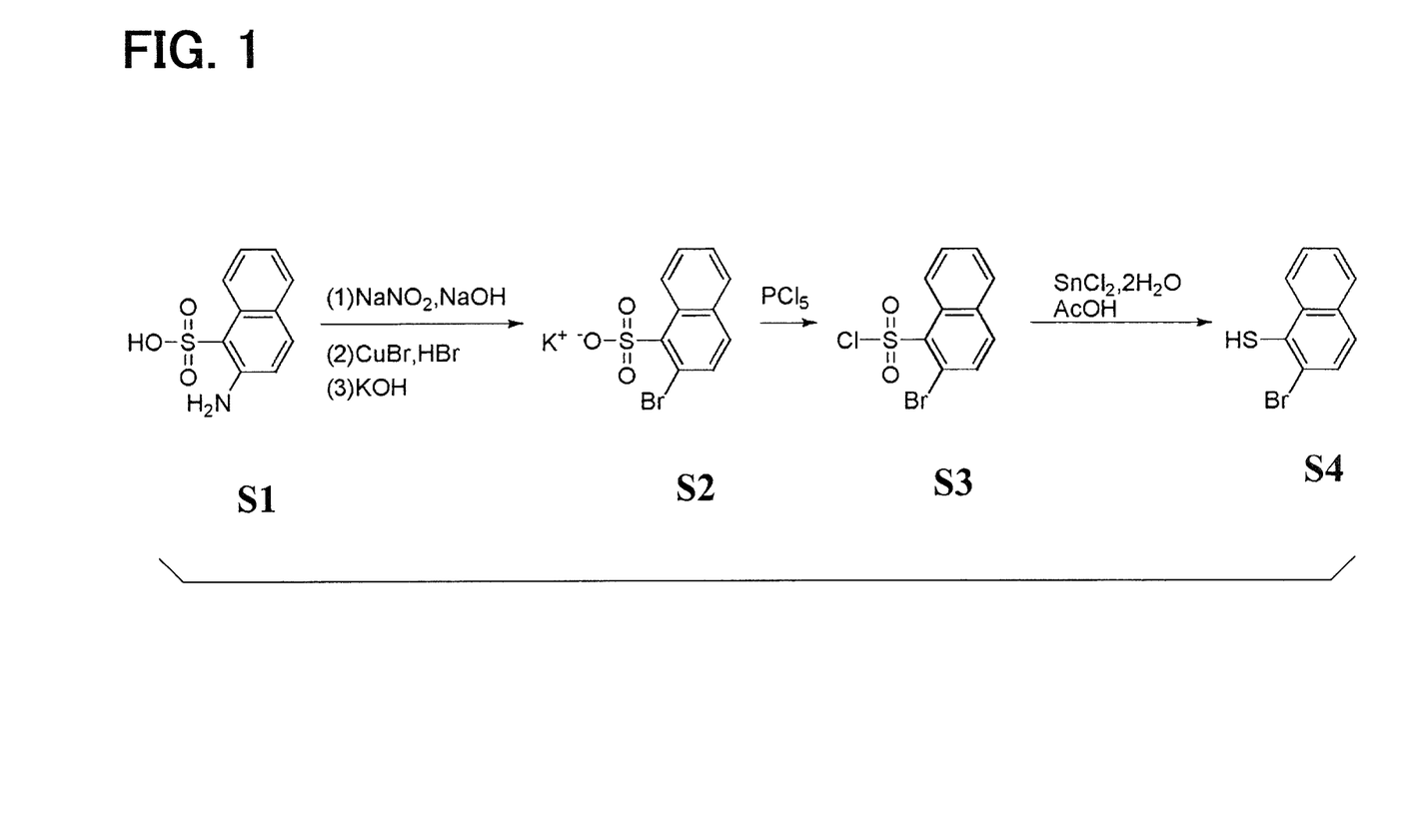
FIG. 1 is a diagram illustrating a method of synthesizing 2-bromo-1-mercaptonaphthalene.
Figure 2:
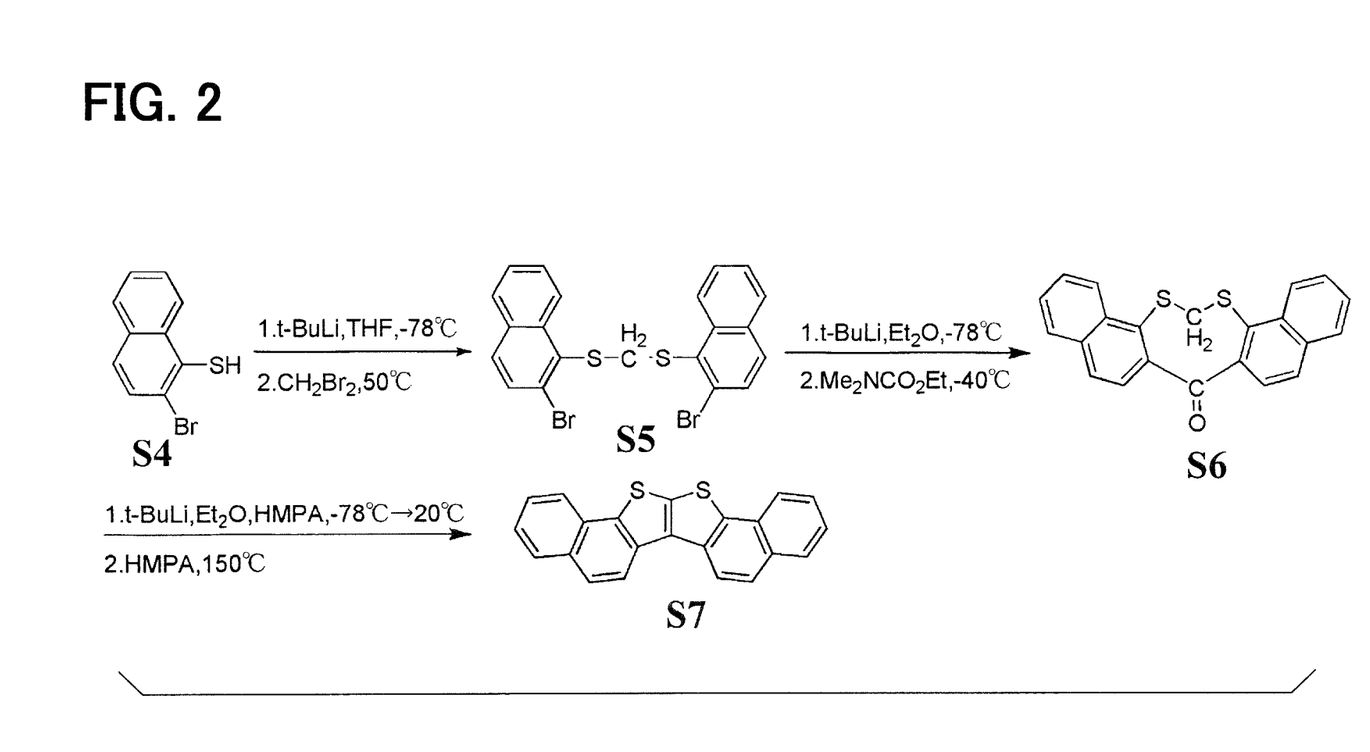
FIG. 2 is a diagram illustrating a method of synthesizing dinaphthothienothiophene.

Dinaphthothienothiophene (organic semiconductor material) is synthesized by a method shown in FIG. 2 using the synthesized 2-bromo-1-mercaptonaphthalene (S4 in FIG. 1).

9.6 g of S4 is dissolved in tetrahydrofuran (made by Wako Pure Chemical Industries, Ltd, 1000 ml) in an Ar atmosphere, cooled to −78° C., added to 16% pentane solution of t-butyllithium (made by Tokyo Chemical Industry CO., LTD, 60 ml), agitated for one hour, added to dibromomethane (made by Tokyo Chemical Industry CO., LTD, 3.6 g), heated to 50° C., agitated for five hours, and refined. Thus, 6 g of S5 in FIG. 2 is obtained.

Next, S5 is dissolved in diethyl ether (made by Wako Pure Chemical Industries, Ltd, 500 ml), cooled to −78° C., added to 16% pentane solution of t-butyllithium (36 ml), agitated for one hour, added to methyl N,N-dimethylcarbamate (1.5 g, prepared by a method disclosed in JP-A-2010-53057, the contents of which are incorporated herein by reference), heated to −40° C., agitated for four hours, and refined. Thus, 3 g of S6 in FIG. 2 is obtained.

Finally, S6 is dissolved in a mixture of diethyl ether (400 ml) and hexamethylphosphoric triamide (made by Tokyo Chemical Industry CO., LTD, 100 ml), cooled to −78° C., added to 16% pentane solution of t-butyllithium (5.6 ml), agitated, heated to a room temperature gradually, agitated for two hours, added to purified water at 0° C., heated to 150° C. after removal of diethyl ether under reduced pressure, agitated for one hour, and refined. Thus, 1 g of dinaphthothienothiophene (S7 in FIG. 2) is obtained.

3. Manufacture of a Thin-Film Transistor

A thin-film transistor (organic semiconductor device) is manufactured by the following processes 1-4 using the synthesized dinaphthothienothiophene.

(Process 1)

Figure 3A:
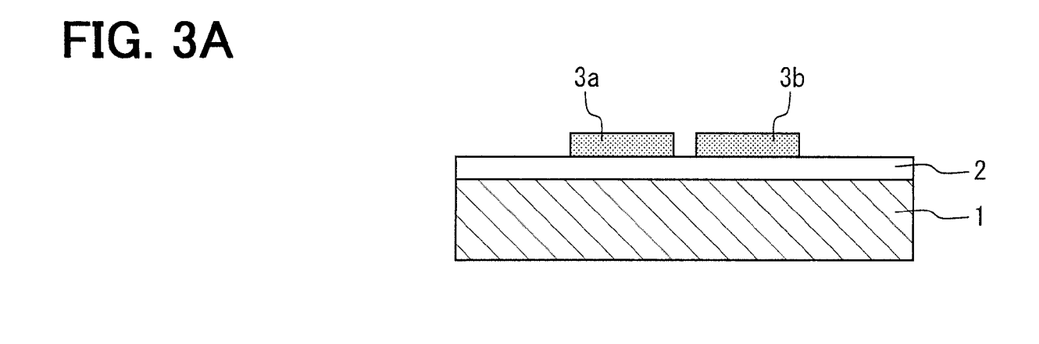
FIG. 3A is a diagram illustrating a cross-sectional view, taken along the line IIIA-IIIA in FIG. 3B, of a substrate of a thin-film transistor according to an embodiment of the present invention.
Figure 3B:
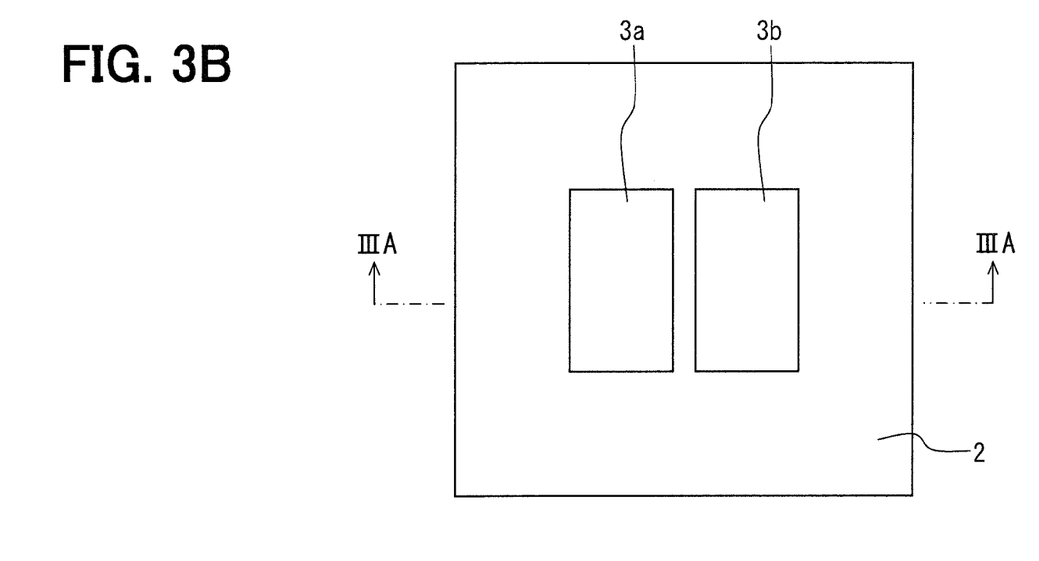
FIG. 3B is a diagram illustrating a top view of the substrate.

An N-type silicon (Si) wafer is used as a substrate 1. A surface of the substrate 1 is thermally oxidized to form a silicon oxide ($SiO_2$) layer (gate insulation layer 2) having a thickness of 200 nm and then is cleaned.

Next, a titanium (Ti) layer having a thickness of 5 nm and a gold (Au) layer having a thickness of 50 nm are successively formed on the gate insulation layer 2 by a resistance-heating vacuum evaporation method.

(Process 2)

A novolak resin-based photoresist is applied to the surface formed in the process 1. Then, the photoresist is patterned into a predetermined pattern by exposure and development using a photo mask. Then, the gold (Au) layer is etched by using a special etchant containing potassium iodide and iodine, and the titanium (Ti) layer is etched by using hydrofluoric acid (200-fold dilution). Then, the resist layer is removed by using special resist stripping solution.

Thus, a source electrode 3a and a drain electrode 3b, which are made from a stacked layer of the titanium (Ti) layer and the gold (Au) layer, are formed.

FIG. 3A is a diagram illustrating a cross-section view of the substrate 1 in this condition, taken along the line IIIA-IIIA in FIG. 3B. FIG. 3B is a diagram illustrating a top view of the substrate 1. FIGS. 3A and 3B illustrates the substrate 1 in a simple manner. Therefore, details such as a thickness ratio may not be accurate.

(Process 3)

The surface of the substrate 1 is cleaned by using an ozonation apparatus. Then, phenethyl self-assembled monolayer is formed on the surface of the gate insulation layer 2 by immersing the substrate 1 in solution in which phenethylsilane compound (β-phen:$C_6H_5(CH_2)_2SiCl_3$) is dispersed in toluene.

(Process 4)

Figure 4A:
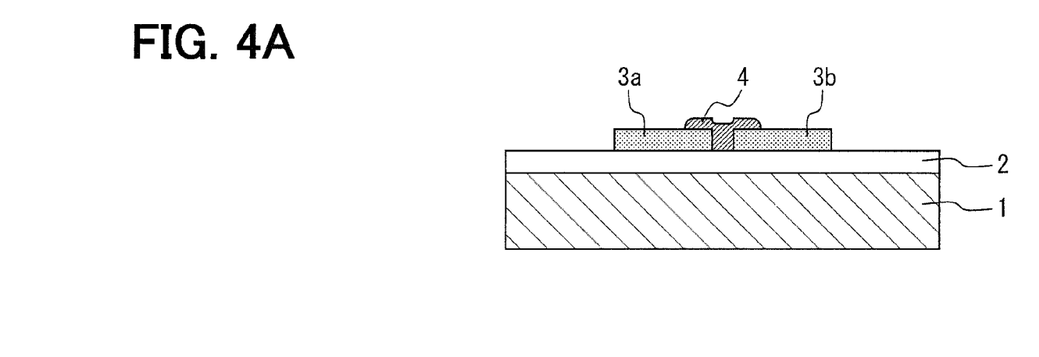
FIG. 4A is a diagram illustrating a cross-sectional view, taken along the line IVA-IVA in FIG. 4B, of the thin-film transistor.
Figure 4B:
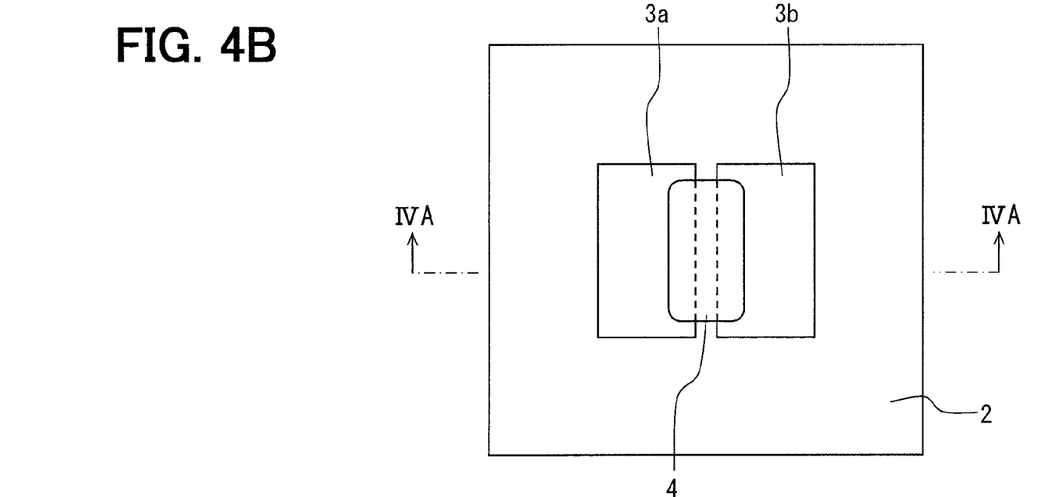
FIG. 4B is a diagram illustrating a top view of the thin-film transistor.

As shown in FIGS. 4A and 4B, a layer (organic semiconductor layer 4) made of dinaphthothienothiophene is formed on the surface of the substrate 1 to straddle between the source region 3a and the drain electrode 3b. Thus, the thin-film transistor is manufactured. The organic semiconductor layer 4 is formed by a resistance-heating method performed by using a shadow mask under vacuum pressure of 3×10E-4 Pa. The organic semiconductor layer 4 is deposited to a thickness of 50 nm at a rate of 0.05 nm/s.

4. Evaluation of a Thin-Film Transistor

A mobility, a threshold voltage, and an On/Off ratio of the thin-film transistor (hereinafter called the "embodiment's thin-film transistor") manufactured in the above manner is measured by operating the embodiment's thin-film transistor as a P-type transistor. A gate electrode is e N-type silicon (Si) wafer (substrate 1), and an active layer is the organic semiconductor layer 4. Further, the same measurement is conducted by using the same embodiment's thin-film transistor after the embodiment's thin-film transistor is stored for about one month at room temperature in the atmosphere. Further, the same measurement is conducted by using another embodiment's thin-film transistor (another sample) immediately after the other embodiment's thin-film transistor is manufactured and after the other embodiment's thin-film transistor is stored for about one month at a temperature of 100° C. in the atmosphere. Results of these are shown in FIG. 5 and FIG. 6.

As a comparison example, a thin-film transistor (hereinafter called the "comparison example's thin-film transistor") is manufactured by using pentacene instead of dinaphthothienothiophene in the process 4. The same measurement as conducted for the embodiment's thin-film transistor is conducted for the example's thin-film transistor. Results of these are shown in FIG. 5 and FIG. 6.

Figure 5:
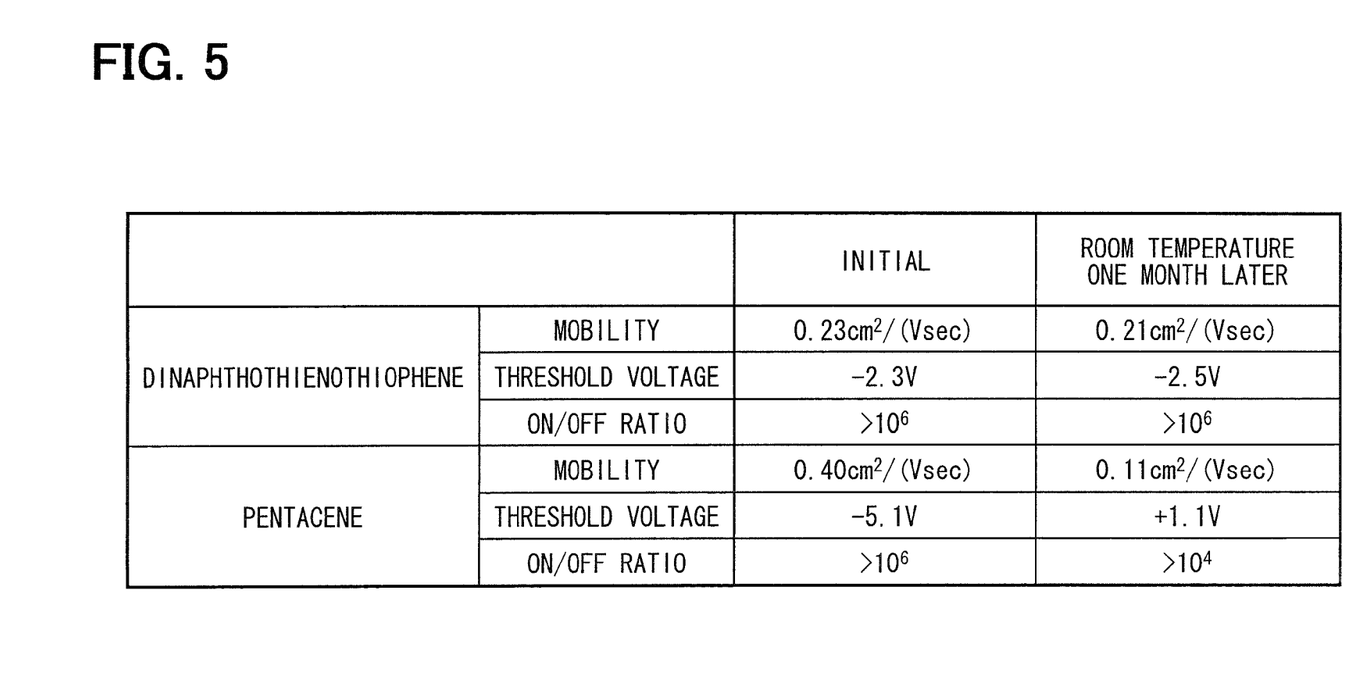
FIG. 5 is a table illustrating a result of evaluation of the thin-film transistor under a first condition.
Figure 6:
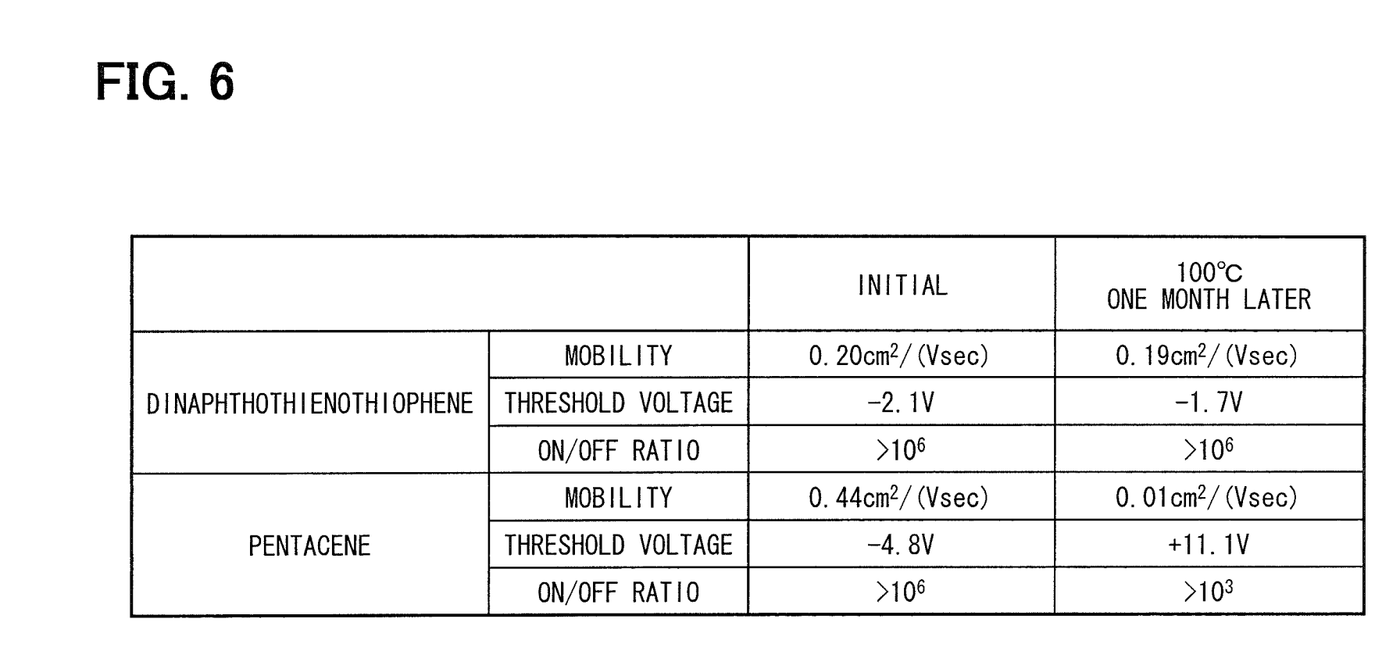
FIG. 6 is a table illustrating a result of evaluation of the thin-film transistor under a second condition.

As is clear from FIG. 5 and FIG. 6, characteristics (mobility, threshold voltage, and On/Off ratio) of the embodiment's thin-film transistor are not much degraded, after the embodiment's thin-film transistor is stored for about one month at room temperature in the atmosphere or stored for about one month at a temperature of 100° C. in the atmosphere. In contrast, characteristics of the comparison example's thin-film transistor are much degraded, after the comparison example's thin-film transistor is stored for about one month at room temperature in the atmosphere and stored for about one month at a temperature of 100° C. in the atmosphere.

It is noted that each of the embodiment's thin-film transistor and the comparison example's thin-film transistor has a channel width of 1800 μm and a channel length of 10 μm. A carrier mobility is estimated from a relational expression (mathematical expression 1) between a gate voltage and a drain current in the saturation region.

$$I_D = \frac{W}{2L}\mu\varepsilon_i\varepsilon_0(V_g - V_{th})^2$$

In the above (mathematical expression 1), $I_D$ represents the drain current, W represents the channel width, L represents the channel length, $\varepsilon_i$ represents a permittivity of the gate insulation layer 2, $\varepsilon_0$ represents a vacuum permittivity, $V_g$ represents the gate voltage, and $V_{th}$ represents the threshold voltage.

What is claimed is:

1. A compound represented by the following formula (1):

wherein X is a chalcogen atom,
wherein Z is carbon or an aromatic ring structure having at least one sulfur, at least one oxygen, or at least one nitrogen in an aromatic ring to which a substituent is capable of being attached,
wherein n is an integer of 1 to 3, and
wherein $R_1$ and $R_2$ are independently selected from a hydrogen atom, a halogen atom, a straight, branched, or cyclic alkyl group, a straight, branched, or cyclic alkoxy group, and a substituted or unsubstituted aryl group.

2. The compound according to claim 1,
wherein X is oxygen or sulfur,
wherein Z is a benzene ring, and
wherein n is 1.

3. The compound according to claim 1, wherein the compound is represented by the following formula (2), and wherein $R_1$ and $R_6$ are independently selected from a hydrogen atom, a halogen atom, a straight, branched, or cyclic alkyl group, a straight, branched, or cyclic alkoxy group, and a substituted or unsubstituted aryl group.

4. The compound according to claim 1,
wherein the compound is represented by the following formula (3), and wherein $R_1$-$R_6$ are independently selected from a hydrogen atom, a halogen atom, a straight, branched, or cyclic alkyl group, a straight, branched, or cyclic alkoxy group, and a substituted or unsubstituted aryl group.

5. A thin film comprising the compound of claim 1.

6. A semiconductor device comprising the thin film of claim 5.

* * * * *